US00PP24809P3

(12) United States Plant Patent
Wheeler et al.

(10) Patent No.: US PP24,809 P3
(45) Date of Patent: Aug. 26, 2014

(54) BLUEBERRY PLANT NAMED 'BB05-274MI-139'

(50) Latin Name: *Vaccinium corymbosum*
Varietal Denomination: BB05-274MI-139

(71) Applicant: Berry Blue, LLC, Grand Junction, MI (US)

(72) Inventors: Edmund J. Wheeler, Holland, MI (US); James F. Hancock, East Lansing, MI (US)

(73) Assignee: Berry Blue, LLC, Grand Junction, MI (US)

( * ) Notice: Subject to any disclaimer, the term of this patent is extended or adjusted under 35 U.S.C. 154(b) by 49 days.

(21) Appl. No.: 13/653,209

(22) Filed: Oct. 16, 2012

(65) Prior Publication Data

US 2014/0109269 P1 Apr. 17, 2014

(51) Int. Cl.
*A01H 5/00* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP9,834 | P | 3/1997 | Lyrene |
| PP10,675 | P | 11/1998 | Lyrene |
| PP11,807 | P2 | 3/2001 | Lyrene |
| PP11,829 | P2 | 4/2001 | Lyrene |
| PP12,165 | P2 | 10/2001 | Lyrene |
| PP15,103 | P3 | 8/2004 | Hancock |
| PP15,146 | P3 | 9/2004 | Hancock |
| PP16,333 | P3 | 3/2006 | Lyrene |
| PP16,404 | P3 | 4/2006 | Lyrene |
| PP18,138 | P3 | 10/2007 | Nesmith |
| PP19,503 | P3 | 11/2008 | Lyrene |
| PP20,027 | P3 | 5/2009 | Lyrene |
| PP21,881 | P3 | 4/2011 | Patel |
| PP22,692 | P3 | 5/2012 | Nesmith |
| PP22,778 | P3 | 6/2012 | Wright et al. |

*Primary Examiner* — Annette Para
(74) *Attorney, Agent, or Firm* — Graybeal Jackson LLP

(57) ABSTRACT

A new and distinct cultivar of blueberry plant named 'BB05-274MI-139' as described and shown herein. 'BB05-274MI-139' is a new and distinct high chill tetraploid Northern highbush blueberry (*Vaccinium*) variety of ancestry based largely on *V. corymbosum* with a limited number of genes from *V. angustifolium*. It is a productive late season ripening variety that ripens approximately at the same time as Elliott, and 25 days after Bluecrop. 'BB05-274MI-139' provides a very good yield potential, very good plant vigor, fruit quality and firmness, as well as characteristics suitable to mechanical harvesting, and very good flavor and texture.

3 Drawing Sheets

BACKGROUND AND SUMMARY

Blueberries are a well-known fruit enjoyed by many throughout the world. One example of an existing, patented blueberry variety is Liberty, U.S. Plant Pat. No. 15,146. Another example of an existing, patented blueberry variety is Elliott, unpatented.

Compared to Liberty, 'BB05-274MI-139' matures approximately 10 days later. The fruit shape of 'BB05-274MI-139' is rounder, larger, and slightly darker blue, and the bush shape of 'BB05-274MI-139' is more spreading than Liberty.

Compared to Elliott, the maturity of 'BB05-274MI-139' is 2-3 days later. The fruit shape of 'BB05-274MI-139' is slightly rounder, and the bush shape is more upright compared to Elliott. 'BB05-274MI-139' has fruit size that is much larger than Elliott.

The present cultivar, 'BB05-274MI-139', provides one or more advantages compared to these and/or other blueberry varieties.

BRIEF DESCRIPTION OF THE PHOTOGRAPHS

DETAILED DESCRIPTION

Figure 1:
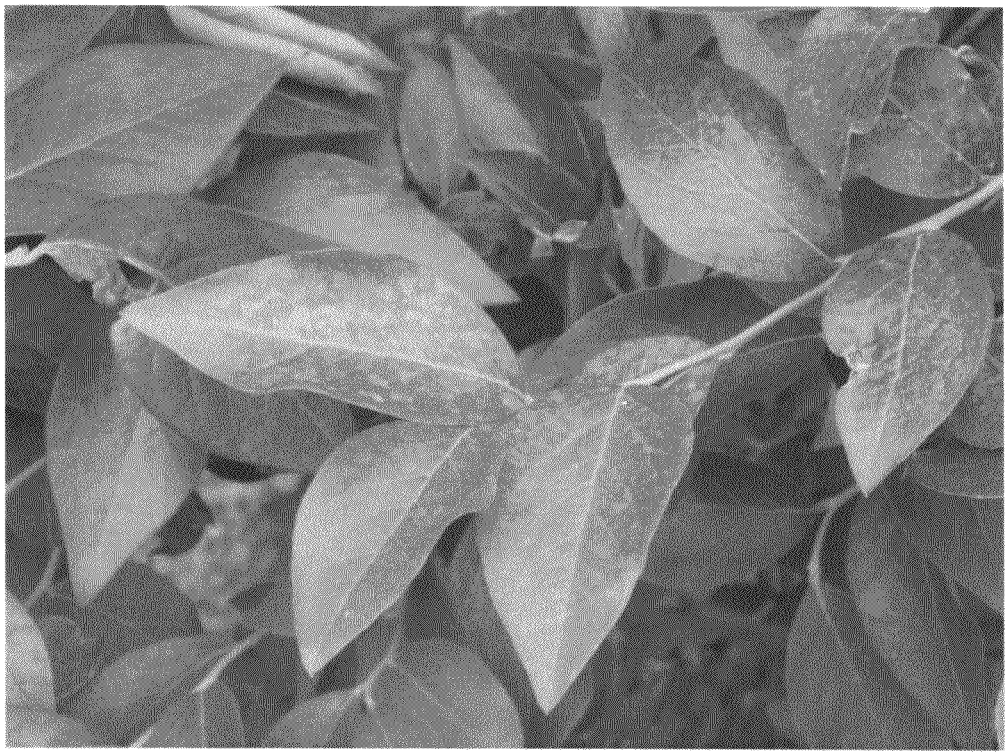
FIG. 1 is a close-up photograph taken in July 2012 of the Blueberry cultivar 'BB05-274MI-139', showing mature leaves and also showing the shape and color of the leaves as well as petiole size and color, serrated leaf margins, and venation.
Figure 2:
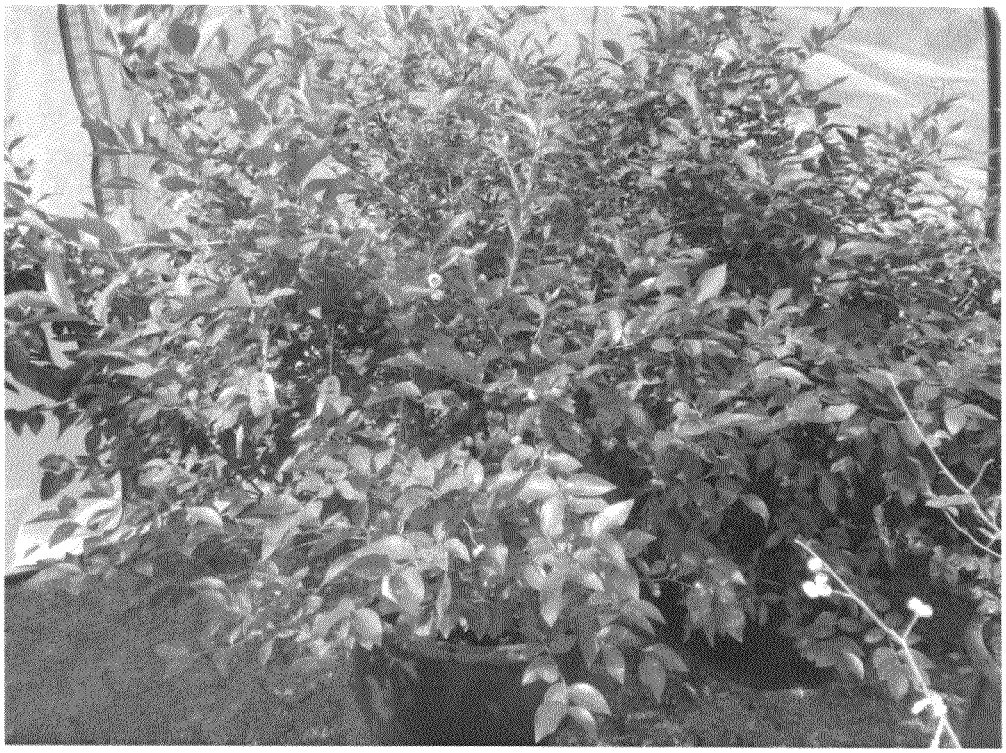
FIG. 2 is a photograph taken in July 2012 of the Blueberry cultivar 'BB05-274MI-139', showing a 6 year old bush in pot, and showing the bush shape, branching habit, color of leaves, and fruit presentation of the variety.
Figure 3:
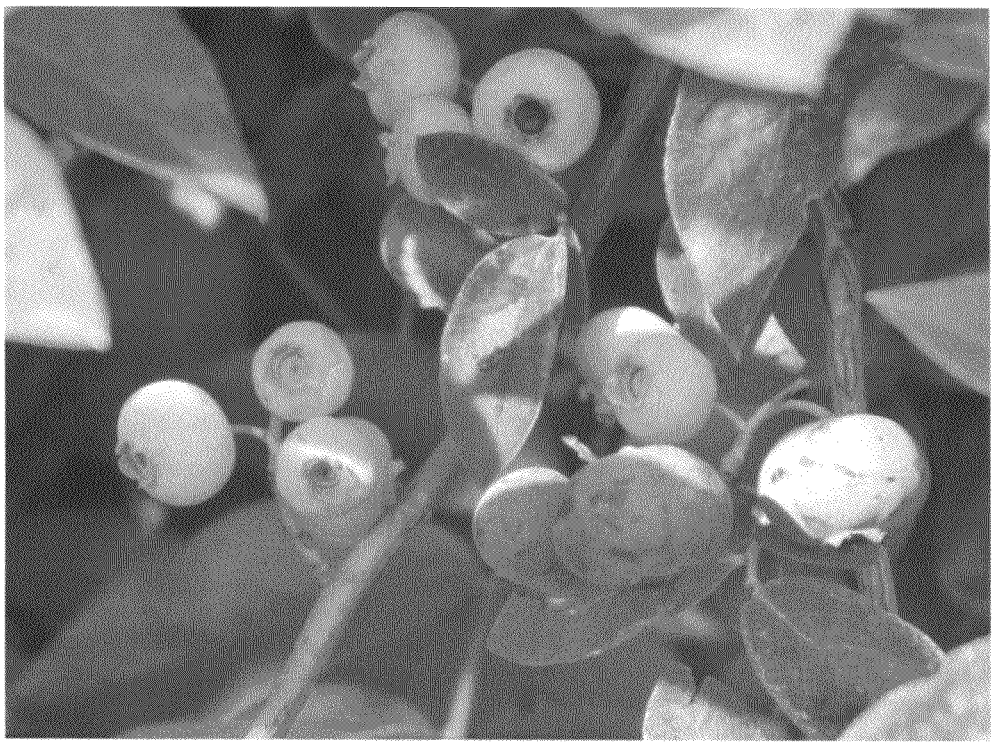
FIG. 3 is a close-up photograph taken in July 2012 of the Blueberry cultivar 'BB05-274MI-139', showing a fruit cluster with ripe and unripe fruit, and also showing shape, calyx, pedicel, peduncle and cluster density of the fruit.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely from specimen plants grown near Grand Junction in 2011 and 2012. Data were obtained on plants that were 7 years old.

Cultivar name: 'BB05-274MI-139'.

Classification:

*Family*.—Ericaceae.

*Botanical name*.—*Vaccinium corymbosum*.

*Common name*.—Blueberry.

Parentage:

*Female parent*.—Brigitta (open pollinated selection of Lateblue unpatented). U.S. Plant Pat. No.: none. Compared to Brigitta, 'BB05-274MI-139' has a maturity date that is 17 days later. BB05-274MI-139 has a slightly darker, rounder and much firmer berry. 'BB05-274MI-139' also has a more spreading bush shape and the leaf margins of 'BB05-274MI-139' are serrated while Brigitta is entire.

*Male parent*.—Nelson (Bluecrop unpatented×G107 unpatented). U.S. Plant Pat. No.: none. Compared to Nelson, 'BB05-274MI-139' matures 17 days later. 'BB05-274MI-139' has a slightly larger, more firm berry than Nelson. Also, the leaf margins of 'BB05-274MI-139' are serrated while Nelson is entire, and the bush shape of 'BB05-274MI-139' is more upright than Nelson.

BB06-507MI-15 was created from a cross in 2006 in a greenhouse in Holland, Mich. Emasculated flowers of Draper were hand pollinated with pollen from Brigitta. Seed was germinated, and plants were grown for 18 months and then planted in a seedling evaluation plot near Muskegon, Mich. in 2007. The plant was evaluated for 3 years and first selected in 2010, based on excellent and desirable fruit and morphological characteristics—maturity date, bush habit and vigor, berry quality, flavor, and storage ability. The bush was dug from the field in October 2011 and transplanted into a pot and placed in a virus-free screened greenhouse. Additional plants have propagated by softwood cuttings and tissue culture and have retained the original characteristics. Five and ten bush advanced trials have been planted in Grand Junction, Gobles, and South Haven, Mich.

'BB05-274MI-139' was first asexually propagated by softwood cuttings in 2010 in Grand Junction, Mich. 'BB05-274MI-139' was also asexually propagated by micropropagation by tissue culture beginning in 2010 and produced cloned plants. The propagated plants from softwood cuttings and tissue culture have retained the original characteristics. The variety roots readily from softwood cuttings and tissue culture microshoots.

Field observations were made in 2012 on a mature 7-year old plant located in Grand Junction, Mich. Laboratory analysis of fruit characteristics were also done in Grand Junction.

General comments: 'BB05-274MI-139' is a new and distinct high chill tetraploid Northern highbush blueberry (*Vaccinium*) variety of ancestry based largely on *V. corymbosum* with a limited number of genes from *V. angustifolium*. 'BB05-274MI-139' is a productive late season ripening variety that ripens approximately at the same time as Elliott, and 25 days after Bluecrop. 'BB05-274MI-139' is characterized as having large, very firm fruit of medium light blue color with a very small and dry picking scar. The fruit is well exposed on a vigorous medium upright plant. Due to a medium sized crown, a loose berry cluster, concentrated ripening, firm and easily detached fruit, the variety displays characteristics suitable for mechanical harvesting. It is intended for areas that successfully grow high chill Northern highbush varieties. Ripe fruit are large, typically 2.5 grams/berry. The mean date of flowering in southern Michigan is approximately May 5. Frost protection may be needed for successful pollination and fruit set. Winter chill requirement for successful flowering and leafing is at least 1000 hours below 7° C. The mean ripening date is August 5. Fruit shape is oblate with a medium high amount of waxy bloom that is persistent following handling. It has very good flavor, balanced between medium levels of sweetness and acidity with a crunchy and juicy texture. It has above average storage ability in refrigeration of 3-4 weeks. 'BB05-274MI-139' provides a very good yield potential, very good plant vigor, fruit quality, flavor and firmness, as well as characteristics suitable to mechanical harvesting, and very good flavor and texture.

References to color refer to The Pantone Book of Color, Eisemann and Herbert, Harry N. Abrams, Inc. Publishers, New York, ISBN 0-8109-3711-5, 1990.

SpectraMagic NX Model CR410, Konica Minolta, Japan.

Morphological characteristics reference: Plant Systematics, Jones and Luchsinger, 2 Ed., McGraw Hill, New York, ISBN 0-07-032796-3, 1986.

Firmness readings—BioWorks FirmTec2, Wamena, Kans.

Average size information: Large bush, spreading shape, 7 year old plant 140 cm height, 170 cm width, height/width ratio 0.8:1.

Growth: Excellent.

Productivity: Very good.

Cold hardiness: Leaf and flower buds −26° C., open flowers and fruit −2° C.

Specific features of the variety:

Plant:

*Growth habit*.—Medium upright.

*Plant width*.—170 cm.

*Plant height*.—140 cm.

*Spread*.—150 cm.

*Productivity*.—6-7 lbs per mature bush.

*Cold hardiness/tolerance*.—Leaf and flower buds −26° C., flowers and fruit −2° C.

*Chilling requirement*.—1000+ hours below 7° C.

*Canes*.—Well branched, 15-18 canes/bush, 50-55 cm range; medium high number of laterals. Mature cane color — Pantone Gray Sand 13-1010.

*Fruiting wood*.—Smooth, immature winter color — Pantone Fall Leaf 15-1132; immature summer color — Pantone Apple Green 15-0543.

*Surface texture of new wood*.—Smooth.

*Mature canes*.—Circular, 12 mm width.

*Time of beginning of leaf bud burst* (*include location*(*s*)).—April 20 (Grand Junction, Mich.).

*Time of beginning of flowering* (*include location*(*s*)).—May 5 (Grand Junction, Mich.).

*Time of fruit ripening* (*include location*(*s*)).—August 5 (Grand Junction, Mich.).

*Disease resistance/susceptibility*.—None claimed.

Foliage:

*Leaf color*.—Upper — Pantone Cypress 18-0322; lower — Pantone Peridot 17-0336.

*Leaf arrangement*.—Alternate.

*Leaf margins*.—Serrated.

*Leaf venation*.—Pinnate.

*Leaf apices*.—Acute.

*Leaf bases*.—Acute.

*Vein and petiole colouration*.—Pantone Herbal Garden 15-0336.

*Petiole length*.—3 mm.

*Leaf dimensions*.—Overall shape: 49 cm-77 cm range, average 68 cm. Width: 26 cm-36 cm range, average 31 cm.

*Leaf margins*.—Serrated, small glands in indentations.
*Leaf surface*.—Glaborous.

Flower:

*Flower shape*.—Elongate urceolate.
*Flower bud number*.—High.
*Flowers per cluster*.—8-9.
*Flower fragrance*.—Sweetly floral.
*Corolla color*.—Pantone Snow White 11-0602.
*Corolla length*.—9 mm.
*Corolla aperture width*.—5 mm.
*Flower peduncle*.—17-20 mm.
*Color*.—Pantone Cedar 16-0526.
*Flower pedicel*.—10 mm.
*Color*.—Pantone Cedar 16-0526.
*Calyx* (*with sepals*).—2 mm.
*Color*.—Pantone Cedar 16-0526.
*Stamen*.—Length: 7 mm.
*Number per flower*.—10.
*Filament color*.—Pantone Caramel 16-1439.
*Style*.—7 mm, top of ovary to stigma tip.
*Color*.—Pantone Mosstone 17-0525.
*Pistil*.—5 mm.
*Ovary color*.—Pantone Mosstone 17-0525.
*Anther*.—Length: 4 mm.
*Number*.—10.
*Color*.—Pantone Caramel 16-1439.
*Pollen*.—Abundance: Medium high. Color: Pantone Vanilla 12-0712.

Fruit:

*Date of* 50% *maturity*.—August 1 (Grand Junction, Mich.).
*Yield*.—6-7 lbs/bush.
*Berry color*.—With wax: Pantone Silver Lake Blue 17-4030, SpectraMagic (L, a, b) 44.12, 0.69, −3.64. With wax removed: Pantone Majolica Blue 19-4125.
*Berry flesh color*.—Pantone Frozen Dew 13-0513.
*Berry surface wax abundance*.—Medium-heavy, persistent.
*Calyx*.—Width — 8 mm; depth — 3 mm; shape — 5 lobed; small ridging of 1 mm lobes.
*Berry weight*.—2.5 grams/berry.
*Berry size diameter*.—17 mm width, 13 mm height, Aspect (H/W) — 0.8.
*Berry shape*.—Oblate.
*Cluster density*.—Loose.
*Detachment force*.—Easy.
*Self-fruitfulness*.—Good; cross pollination will enhance berry size and yield.
*Fruit stem scar*.—Very small, <1 mm, dry.
*Berry firmness*.—Firm; FirmTec2 reading — 217 g/mm$^2$.
*Berry sweetness*.—Medium Brix° 11.9.
*Berry acidity*.—Medium high, TA — 0.95.
*Berry flavor and texture*.—Good flavor, good balance of sweetness and acidity, slightly crunchy and juicy texture.
*Suitability for mechanical harvesting*.—

Seed:

*Seed abundance in fruit*.—Medium, 10-15 per berry.
*Seed color*.—Pantone Narcissus 16-0950.
*Seed dry weight*.—NA.
*Seed size*.—Medium, 1.5 mm.

Possible typical market uses: Fresh market, processing into jams, puree, yogurt.

Storage quality: Very good, 3-4 weeks in refrigerated storage.

What is claimed is:

1. A new and distinct cultivar of Blueberry plant named 'BB05-274MI-139' as described and shown herein.

* * * * *